United States Patent [19]
Ma

[11] Patent Number: 5,532,166
[45] Date of Patent: Jul. 2, 1996

[54] QUANTITATIVE RETINOL ASSAY FOR SERUM AND DRIED BLOOD SPOTS

[76] Inventor: Yinfa Ma, 712 E. Meadow La., Kirksville, Mo. 63501

[21] Appl. No.: 508,353

[22] Filed: Jul. 27, 1995

Related U.S. Application Data

[63] Continuation-in-part of Ser. No. 228,674, Apr. 18, 1994, abandoned.

[51] Int. Cl.[6] ............................ G01N 21/64; G01N 33/50
[52] U.S. Cl. .............................. 436/86; 436/131; 436/172; 436/175
[58] Field of Search .............................. 436/86, 131, 172, 436/175

[56] References Cited

PUBLICATIONS

J. Glover, Fluorescence Assay of Retinol–Binding Holoprotein, *Methods in Enzymology*, 67:282–287 (1980).

HC Furr, A Direct Microassay for Serum Retinol (Vitamin A Alcohol) by Using Size–Exclusion High–Pressure Liquid Chromatography with Fluorescence Detection, *Analytical Biochemistry*, 171:360–365 (1988).

P. Grossman, Application of Free–Solution Capillary Electrophoresis to The Analytical Scale Separation of Proteins and Peptides, *Analytical Chemistrym*, 61:1186–1194 (1989).

Kuhr, Indirect Fluorescence Detection of Native Amino Acids in Capillary Zone Electrophoresis, *Analytical Chemistry*, 60:1832–1834 (1988).

Ma, Fast Minimicrocroassay of Serum Retinol (Vitamin A) by Capillary Zone Electrophoresis with Laser–Excited Fluorescence Detection, *Journal of Chromatography*, 616:31–37 (1993).

*Primary Examiner*—Jeffrey R. Snay
*Attorney, Agent, or Firm*—Zarley, McKee, Thomte, Voorhees & Sease

[57] ABSTRACT

Capillary Zone Electrophoresis (CZE) with laser-excited fluorescence detection has been found to be a fast, easy, and accurate method for directly measuring serum retinol. Due to its small sample requirements, the method may be used for finger-prick analysis.

16 Claims, 6 Drawing Sheets

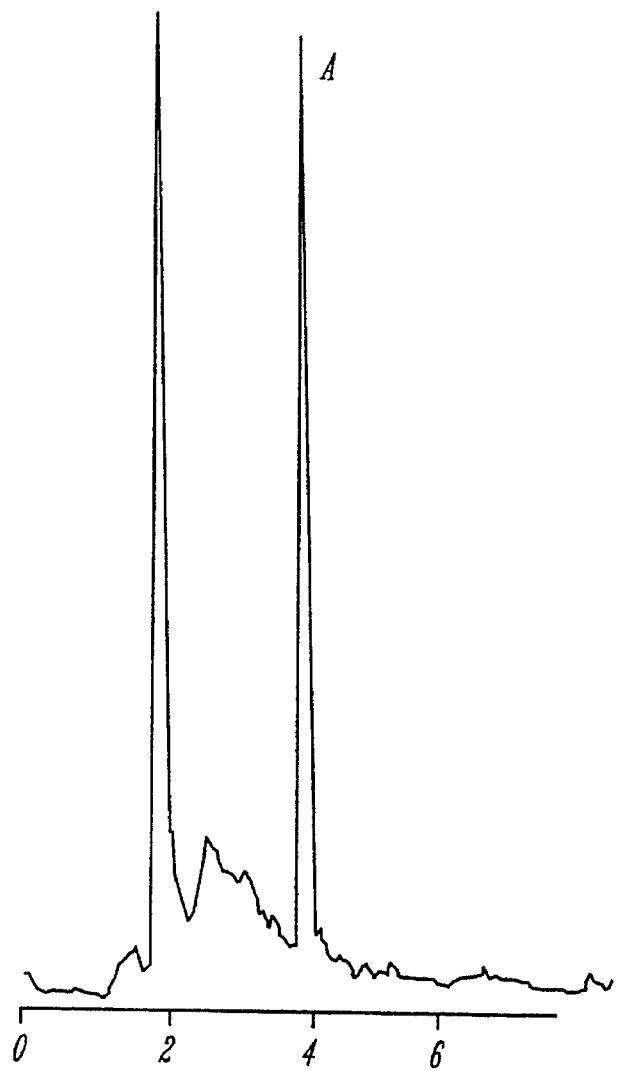
FIG.5　TIME (min.)
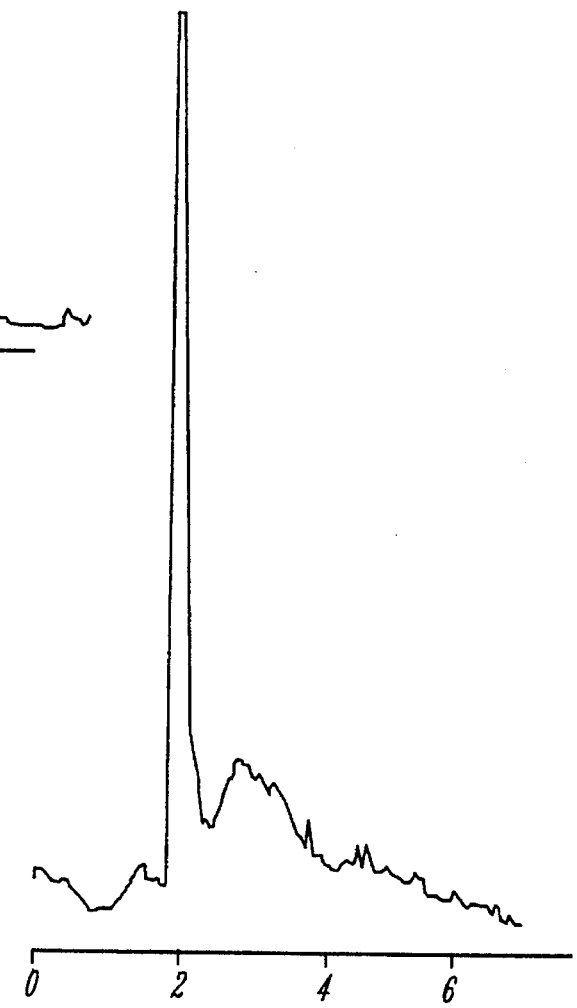
FIG.6　TIME (min.)

QUANTITATIVE RETINOL ASSAY FOR SERUM AND DRIED BLOOD SPOTS

This is a continuation-in-part application of Ser. No. 08/228,674, filed Apr. 18, 1994, now abandoned.

BACKGROUND OF THE INVENTION

As is well-known, vitamin A is extremely important for the health of humans and animals. Among its essential functions are cellular differentiation and vision. Deficiency of Vitamin A can result in adverse effects on reproduction, growth, and the immune response. Vitamin A deficiency can also affect the eyes often resulting in blindness.

On the other hand, high levels of vitamin A can cause serious toxic manifestations; namely teratogenicity, chronic toxicity and acute hypervitaminosis. Some individuals may also show a genetic sensitivity to vitamin A, termed vitamin A intolerance, at intakes not much above those normally ingested. Thus, management of Vitamin A levels can have serious implications.

Presently in Third World nations, many young children are plagued by night blindness and other vitamin A-related diseases. It has been estimated that more than one million become permanently blind each year because of vitamin A deficiency.

Accordingly, for the above reasons, development of a fast and accurate method of measuring vitamin A levels is of international importance. This invention relates to a method of determining vitamin A levels in human blood serum which offers the advantage of smaller blood samples for analysis as well as less time and more simplicity.

Vitamin A (retinol) is normally transported in the blood as a complex with RBP (retinol-binding protein). RBP is a single polypeptide chain with a molecular mass of about 21,000 and has a single binding site for one molecule of retinol. The retinol-RBP further interacts strongly with another protein, plasma transthyretin (TTR or prealbumin) and normally circulates in plasma as a 1:1 complex (molar ratio) with TTR. These complex interactions and association of companion proteins with retinol have made determining retinol levels a difficult, time-consuming task.

The serum retinol concentration is the most commonly used indicator of vitamin A status. The preferred method for analysis of retinol is high-performance liquid chromatography (HPLC). The method involves collection of at least 200 µl of whole blood, centrifugation within hours of collection, and keeping the samples in the cold during transport and storage. In the laboratory, the serum proteins are precipitated and retinol is extracted with organic solvents. The extracts are separated by HPLC and retinol is detected by UV absorbance or fluorescence. The limitations of this method are: (1) a large amount of serum sample (100 µl or more) is needed, which is often difficult to obtain by capillary sampling and represents a large volume from infants, especially for neonates and low-birth-weight infants; (2) once separated from RBP, retinol is light-, oxygen- and heat-sensitive, increasing the likelihood of error during analysis; (3) processing time is relatively long.

Retinol is labile to light, oxygen, and heat, making it difficult to handle, especially when it is removed from the protection of its biological matrices. Extracted retinol decomposes rapidly even at subambient temperature when exposed to normal light.

In contrast, retinol is stable in frozen serum at −70° C. for at least eight years. Retinol itself has a maximum absorbency at 325 nm and fluorescences at 425 nm. However, when retinol is bound to RBP the intensity of the fluorescence is enhanced ten to fourteen-fold and the fluorescence shifts to 465 nm. Additionally, these characteristics of retinol have provided encouragement for methods that would allow a direct determination of retinol in serum.

Current improvements along this vein include a micromethod involving gel-electrophoretic separation of serum, with subsequent estimation of the retinol-RBP complex by fluorimetric scanning of the gel. This method avoids solvent extraction, but is still limited by large sample requirements, long separation times and gel scanning, which make it of limited use for surveys of vitamin A status.

Recently, high performance size-exclusion liquid chromatography (SE-HPLC) with fluorescence detection has been used to measure retinol-RBP in animal and human serum. Compared to previous methods, less serum is required and preliminary sample treatment is avoided. However, a 0.05 ml blood sample is needed for analysis and 20–30 minutes of HPLC separation time is required. In addition, at least 1 ng of retinol-RBP is required for detection. These factors make it difficult to do minimicroassy, especially for babies and young children, where only small blood samples are available.

There is therefore a need in the art for a method to directly measure retinol in blood serum quickly, accurately, and without need for large blood samples.

The primary object of the present invention is, therefore, to develop a method to directly evaluate levels of vitamin A in human blood serum.

It is a further object of the present invention to provide a method to determine vitamin A levels in human blood serum which is accurate, fast, and easy.

It is a still further object of the present invention to develop a method to determine blood serum levels of vitamin A which requires smaller blood samples by use of Capillary Zone Electrophoresis than conventional methods.

SUMMARY OF THE INVENTION

This invention relates to the use of Capillary Zone Electrophoresis (CZE) with fluorescence detection in separating and detecting retinol in human blood serum. Serum taken from a human subject is injected into a capillary for separation along an electrical gradient maintained within the capillary. A buffer maintained at a pH between 7.5 and 10.3 is used to carry the serum through the device. A laser or other device with emission at the 325 nm wave length is used for excitation and the florescence of the vitamin A-retinol binding protein (RBP) complex is then collected and measured.

In this system, the sample size may be from 8 to 10 nl and is injected without any additional sample preparation to purify the retinol. The analysis time for each sample is less than six minutes and subfemtomoles of vitamin A can be easily detected. This methodology also may be used to measure serum retinol levels from a dried blood spot which is dissolved and then subjected to CZE. CZE offers many advantages over the most commonly used method to measure serum retinol, HPLC, which include higher resolution and shorter analysis time. In addition, it requires only a very small amount of sample (nl or pl) and has a very low detection limit (attomoles).

DETAILED DESCRIPTION OF THE DRAWINGS

FIG. 1 is a drawing of an instrumental setup for the CZE analysis of retinol in human serum with laser-excited fluorescence detection.

FIGS. 2A–2E are a series of drawings depicting the influence of buffer pH on the separation and detection of retinol-RBP. pH used: 2(A), pH 7.1; 2(B), pH 7.5; 2(C), pH 8.5; 2(D), pH 10.3; 2(E), pH 11.5. Buffer concentration: 50 mM sodium phosphate +10 mM sodium chloride. A 10 second, +10 KV injection of the serum sample followed by electrophoresis at +24 kV for 5 minutes in a 60 cm (50 μm i.d.) capillary column. Excitation wavelength: 325 nm; fluorescence was monitored at 465 nm (with a bandpass filter). Peak identification: A, retinol-RBP complex.

FIG. 3 is a drawing of a pure retinol-RBP complex electrophoregram. The pH of the running buffer: 7.8. A 30 s, +10 kV injection was used. Other conditions are the same as those in FIG. 2. Peak identification: A, retinol-RBP complex.

FIG. 4 is a drawing of the Electrophoregram for direct injection of serum into the capillary for analysis of Vitamin A. Buffer: 50 mM phosphate, pH 7.8. A 10-s injection at 10 kV of the serum sample or dissolved blood spot sample was followed by electrophoresis at +20 kV for 6 minutes in a 60 cm×50 μm I.D. capillary column. Excitation wavelength: 325 nm; fluorescence was monitored at 465 nm (with a bandpass filter), FIG. 5 shows the Electrophoregram for direct injections of pretreated serum sample. Peak A=retinol-RBP complex. The electrophoretic conditions are the same as those of FIG. 4.

FIG. 6 is a drawing of the Electrophoregram of the blank control (the pretreatment buffer was treated the same way as that of serum sample and injected into the capillary to run an electrophoresis). Electrophoretic conditions are the same as those of FIG. 4.

DETAILED DESCRIPTION OF THE INVENTION

Figure 1:
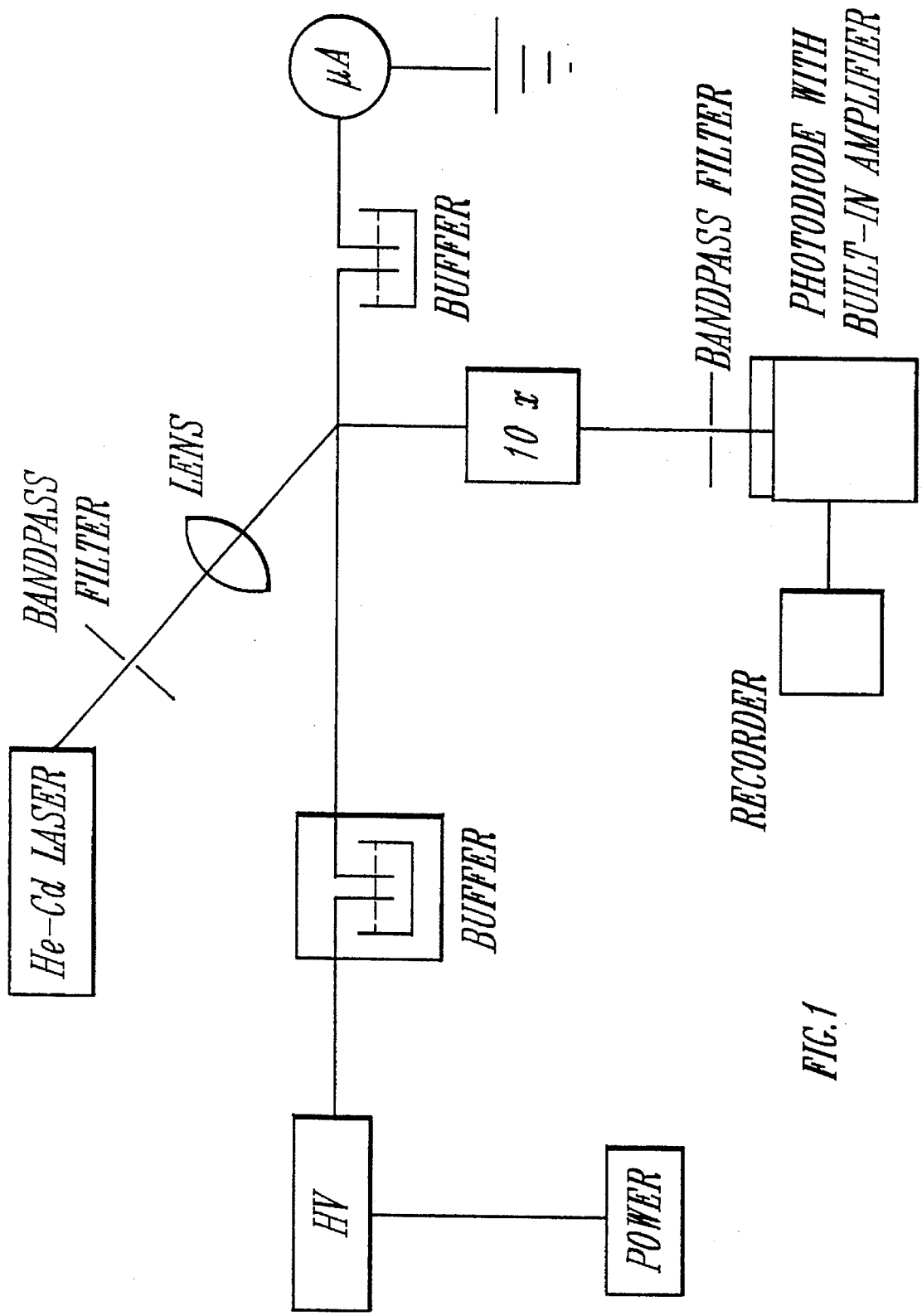
Figure 2A:
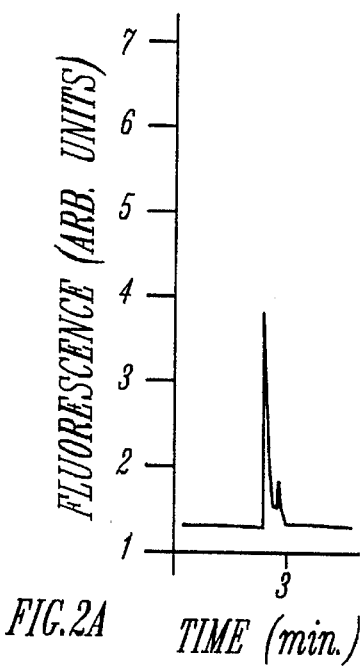
Figure 2B:
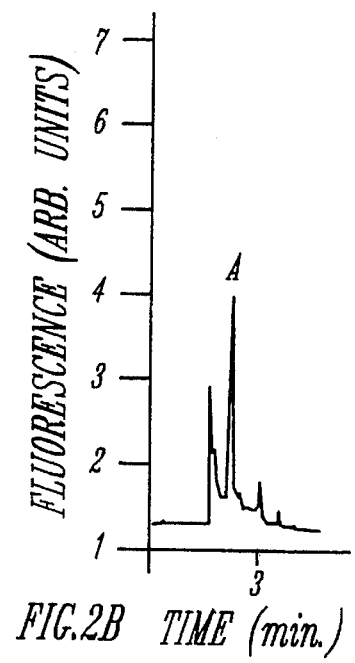
Figure 2C:
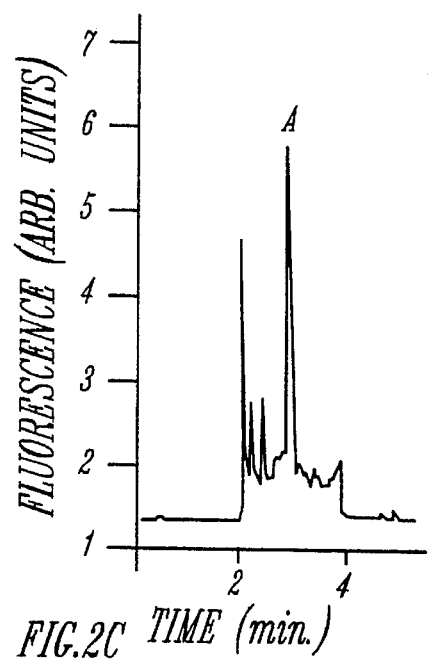
Figure 2D:
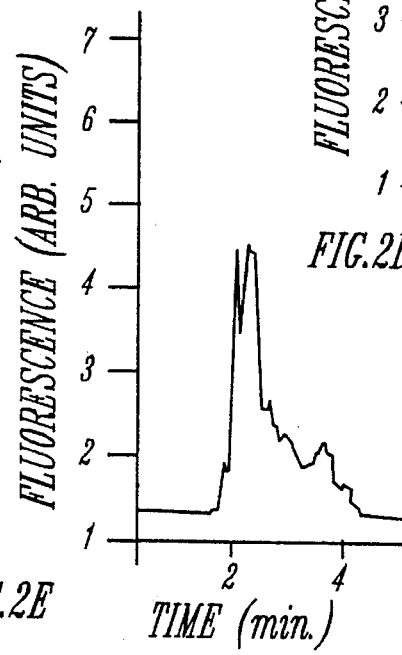
Figure 2E:
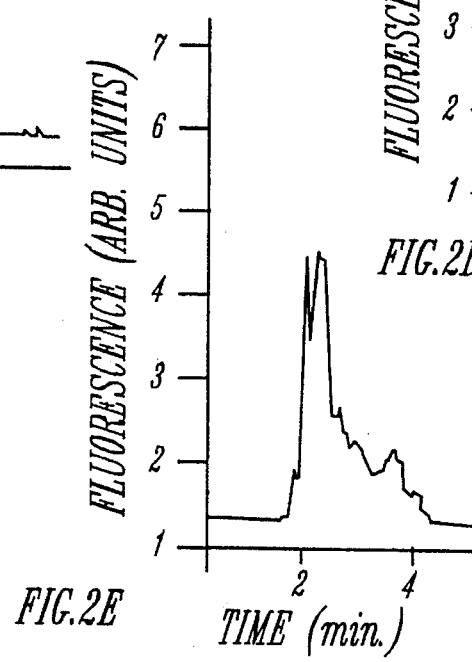

CZE does not require separation of the retinol from the serum prior to its analysis. Because of this, the CZE method is much less time-consuming and easier to use than the HPLC method. In addition, since the CZE method requires only a very small amount of blood sample for analysis, CZE is potentially useful for finger prick vitamin A analysis, especially for babies and young children, as well as dried blood spot analysis which will greatly simplify sample collection. To date no method has been developed using Capillary Zone Electrophoresis to detect serum retinol.

Generally the method is as follows. First a sample of serum from a patient is prepared by centrifugation. The amount of blood taken can be quite small as only 5 to 10 uL of serum is needed. For dried blood spot analysis the blood is spotted onto filter paper which is dried and later dissolved with buffer. The sample is then pre-treated with a urea buffer or any such buffer which includes an agent such as urea which will denature transthyretin (TTR) from the TTR-Retinol-RBP complex without dissociating the retinol-RBP. This extra step not present in traditional protocals was found to be necessary because of problems with sample absorption onto the capillary poor separation and quantitation.

Running buffer then is added to the serum (or dissolved serum). Suitable buffers include any traditional buffer solution known to those of skill in the art and can include borate, tris phosphate, phosphate or any agent which will not react with the retinol. Concentrations of the buffer can be from 30 to 70 mM, and must be adjusted to a pH in the range of from 7.5–10.3 the pH range is critical for the accurate detection of retinol RBP. Buffer is added according to the following proportions which may vary depending on amount of serum. Generally to 10 uL of serum, 200–500 preferably about 300 uL of pretreatment buffer is added. The mixture is filtered to remove larger molecular weight molecules (>30 kDa) and then is ready to be injected into the capillary device with running buffer in an amount of 5–10 nL.

Capillaries are those commonly used in this type of electrophoric separation. Traditionally they are glass or silica with diameters ranging from 25–70 uM. Any polymer coating on the capillary is removed towards the cathodic end to create a detection window. An electrical gradient is set up along the length of the capillary, to establish an electrophoresis device as is known to those of skill in the art.

An emission source such as a laser which will emit radiation at a wavelength of 325 nm is used for excitation and the resulting retinol florescence at 465 nm is amplified for signal detection. A filter is used in a preferred embodiment to reject stray and scattered radiation from the laser head.

A photodiode is used to convert the collected light energy at the filtered wavelength to an electrical signal over time which may be integrated.

An electronic reporting integrator is used to translate the signal into a series of peaks defined by arbitrary units over time. Quantitation of florescence is achieved by comparison of peak areas or peak heights to a standard calibration curve, prepared by determination of detector response (peak height or peak area) to known amounts of retinol analyzed under identical conditions. Peak area is preferred because it is less susceptible to fluctuations due to varying conditions.

When retinol is measured by this method a response is achieved in less than 6 minutes and is linear over the range 0.1–0.6 μg/ml, which is the physiological range in human serum.

The following examples are offered to further illustrate, but not limit the invention. They show the comparison of HPLC versus CEZ analysis, also illustrate the effects that changing the pH of the buffer has on the retinol-RBP complex, as well as the method using a dried blood spot sample.

EXAMPLE I

Reagents:
All chemicals are of analytical reagent grade unless stated otherwise. Deionized water was prepared with a Milli-Q system (Millipore, Bedford, Mass.).
Running Buffer Preparation:
The running buffer is composed of 50 mM $Na_2HPO_4$, the pH is adjusted to 7.8 with 1.5M $H_3PO_4$. The running buffer is filtered with 0.45 μm membrane and degassed before using.

Serum Samples:

Actual samples of serum were also obtained. Frozen human serum was obtained from the Department of Nutritional Science in the University of Connecticut (Storrs, Conn., USA). Fresh human blood samples were obtained from volunteers in Grim-Smith Hospital (Kirksville, Mo., USA). All the blood samples were centrifuged for 7–8 minutes at 3700 rpm (approximately 1500 g) to separate red blood cells from the serum. Serum was then directly injected into the high-performance capillary zone electrophoresis (HPCZE) for analysis. Unused serum was kept at −20° C. until analysis.

Pretreatment of Serum Samples:

To 10μ of serum, 290μ of ice-cold sample pretreatment buffer (50 mM $Na_2 HPO_4$+6M urea pH 7.8) was added and the mixture was then mixed well on a Vortex mixer (Fisher, St. Louis, Mo., USA). The pretreatment buffer pH had adjusted to 7.8 with 1.5M $H_3PO_4$. The solution was then allowed to stand on ice for 3–5 minutes and 100 μL solution was taken out and put into a Microcon-30 filter unit (Amicon, Inc., Beverly, Mass., USA) (this filter unit allows molecular weight <30 KDa molecules to pass through), and filtered by centrifugation. The filtrate was then ready to be injected into the high performance capillary electrophoresis (HPCE) column for analysis.

Standard Retinol-RBP Preparation:

A standard was used to calibrate the system. Standard Retinol-RBP was prepared using a modification of the method of the Moffa and Krause. First, 10 mg of pure retinol standard was dissolved in 10 ml of absolute ethanol (concentration was 1g/l). 10 μm of standard RBP was dissolved in 5 ml of 0.1M sodium phosphate buffer (pH 7.7). Then 20 μm of retinol standard solution was slowly transferred into 5 ml of standard of RBP solution with appropriate stirring. The retinol-RBP mixture was allowed to stand for 3 hours at 25° C. and was then ready for injection.

Equipment Set-Up:

A Model CZE 1000R high-voltage power supply (Spellman, Plainview, N.Y., USA) was used to supply the electromotive force across the capillary. The anodic high-voltage end of the capillary was isolated in a plexiglass box for safety while the cathodic end was held at ground potential. A 60 cm ×50 μm I.D. fused silica capillary tubing (Polymicro Techniques, Phoenix, Ariz., USA) was used for the separation. The polymer coating was burned off 25 cm from the cathodic end of the capillary to form the detection window.

A Model 4240NB helium-cadmium (He-Cd) laser (Liconix, Santa Clara, Calif., USA) operating at 325 nm was used for excitation. A band-pass filter (250 nm-400 nm) (Ealing, Holliston, Mass.: Model UG-11) was used to reject stray and scattered radiation from the laser head. The laser was focused onto the capillary with a 1 cm focal length lens, and the fluorescence was collected with a 10x microscope objective at a 90° angle to the incident light. The fluorescent image was focused onto a silicon photodiode combined with a build-in amplifier (Hamamatsu, Bridgewater, N.J.; Model HC220-01). Another band-pass filter (400–539 nm) (Ealing, Holliston, Mass.; Model 35-532) is used to isolate the fluorescence (465 nm) from the vitamin A-RBP complex. The voltage from the photodiode was monitored with an autoranging microvolt DMM (Keithley, Cleveland, Ohio; Model 197AZ) and the signal was recorded with a Model C-R3A integrator (Shimadzu, Columbia, Md.).

Pretreatment of the Capillary Column:

Each new capillary column was filled with a 1.0 M sodium hydroxide solution for about 30 minutes to clean the column. The column was then washed with a 0.1M sodium hydroxide followed by deionized water and finally running buffer. The capillary was ready for use thereafter.

Conventional Extraction and HPLC Analysis of Retinol From Serum:

Standard Extraction and HPLC was performed to compare the to methods. HPLC was performed as follows. To 100 μl of the freshly thawed serum from the Department of Nutritional Science was added an equal volume of methanol containing an internal standard (retinyl hexanoate): each sample was extracted three times with an equal volume of hexane. Hexane from combined hexane extracts was evaporated under a gentle stream of argon, and the residue was dissolved in 50 μl 2-propanol-dichloromethane; 20 μl was injected for HPLC analysis. Samples were analyzed by reversed-phase HPLC on a 5-μm Resolve $C_{18}$ column (Waters Assoc., Milford, Mass., USA) using a mobile phase of acetonitrile-dichloromethane-methanol-n-butanol (90:15:10:01), containing 0.1% ammonium acetate, at a flow-rate of 1.0 ml/minute, with detection at 300 nm.

HPCZE Analysis:

Serum samples were injected electrokinetically at 10 kV for 10 seconds (approximately 8–10 nl were injected), and the separation was carried out at 24 kV for 5 minutes. The electrophoretic current was monitored with a multimeter throughout the separation to ensure the reproducibility. After five to seven injections, the capillary required cleaning due to the adsorption of serum proteins on the capillary wall. Cleaning was accomplished by flushing the capillary for 4 minutes with 1M sodium hydroxide, then 2 minutes with deionized water and finally for 2 minutes with running buffer.

Frozen human serum from the Department of Nutritional Science was used to make a calebration curve to quantify serum retinol levels.

Effect of pH on Separation and Signal:

Adsorption of proteins onto the capillary wall is a serious problem when separating proteins by CZE using uncoated silica columns. Performing the separation at a pH above the isoelectric point(pI) of the proteins under investigation is one of the most active ways to minimize protein buildup. In this way the coulombic repulsion between negatively charged proteins and the capillary wall will minimize the protein adsorption. However, the retinol-RBP complex is sensitive to the pH of the buffer, whereby higher pH may cause the retinol-RBP complex to decompose.

In order to optimize the separation and detection of the retinol-RBP complex, a wide range of buffer pH (3–11.5) was investigated and over 15 different pH buffers were tried before the critical pH range was established. At lower pH (2), no retinol-RBP signal was observed. Two phenomena contribute to this observation. First, since the pI of RBP is between 4.4 to 4.8 the retinol-RBP complex was heavily adsorbed onto the capillary when the pH of the buffer was near to or lower than the pI of the RBP. Secondly, the fluorescent intensity of the retinol-RBP complex at this pH is reduced. Both factors have been demonstrated experimentally.

When the pH of the buffer was 6–7.2, only a single peak with a small shoulder was observed. In addition, there was no linear relationship between peak heights or peak areas and retinol-RBP levels for a series of standard samples at low or neutral pH. This may be due to incomplete separation of the serum matrix and retinol-RBP and the partial adsorption of retinol-RBP onto the capillary wall. When the buffer pH was kept at 11.5, the characteristic peak of retinol-RBP disappeared. This was apparently due to the decomposition of retinol-RBP complex. If the buffer pH was kept at 10.3, the retinol-RBP peak was detectable: however, the linearity of the retinol-RBP response of the standard serum samples was very poor due to partial decomposition of the retinol-RBP complex. When the buffer pH was maintained between 7.5 and 8.5, both complete separation of the retinol-RBP complex from other serum components and a linear response for standard serum samples were attained. However, within this pH range, we observed that the fluorescent signal of the retinol-RBP complex was enhanced at higher pH (from 7.8 to 8.5). Therefore, pH 7.8 was employed in this work as an optimized pH to analyze serum samples.

Figure 3:
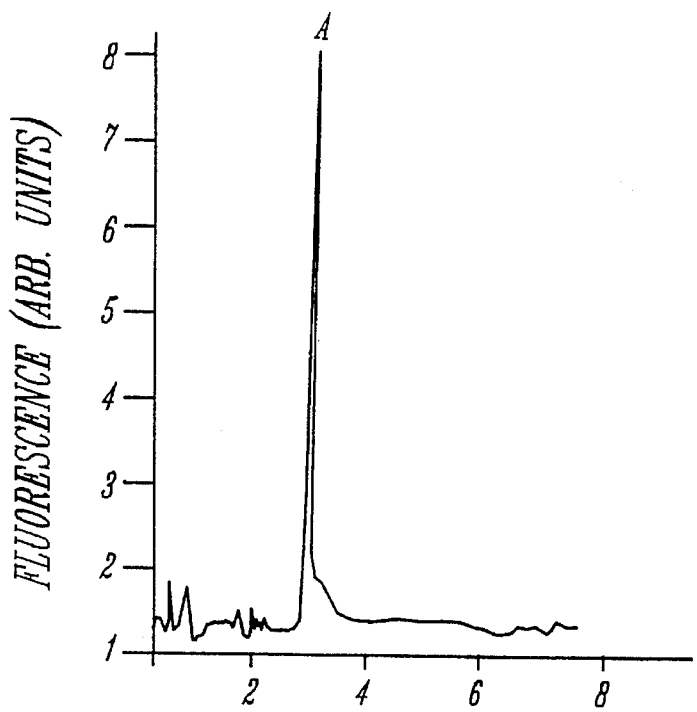

Identification of retinol-RBP Peak:

In order to verify the retinol-RBP peak in the standard serum electropherogram, pure retinol-RBP complex, which was prepared from retinol and isolated human RBP was injected. The results was shown in FIG. 3. The pure retinol-RBP complex migrates as a single peak (A) that exactly matches the peak A in FIG. 2.

Although retinyl esters, as well as very small amounts of unesterified retinol, will be present in chylomicra, their contribution to circulating vitamin A in fasting blood is small (<10%); retinol-RBP is the physiologically important transport form of vitamin A. Retinol-RBP is well resolved from the lipoproteins by these electrophoretic conditions.

Linearity:

Linear response to graded levels of vitamin A in the serum is extremely important in quantitative analysis of vitamin A in human serum. We observed very good linearity between the fluorescence signal (peak height) and the vitamin A concentration of standard serum samples with known concentrations of vitamin A. The response is linear over the range 0.1–0.6 µg/ml which is the physiological range in human serum. The detection limit for this technique is approximately 10 ng/ml of serum (or 10 fg of retinol) at a signal-to-noise of 5:1. In order to make sure the separation conditions are maintained the same, a fresh serum sample was used as a reference, which was injected after several sample injections.

Comparison of HPCZE with HPLC for Vitamin A Analysis:

As an additional verification of the method, a series of frozen serum samples were analyzed with both conventional HPLC and HPCZE. The results from both techniques are listed in Table I.

TABLE I

Comparison of concentrations of retinol (Vitamin A) in human serum samples determined by HPLC and HPCZE

| Serum samples | Concentrations of retinol (ng/mL) | |
| --- | --- | --- |
| | HPLC method[1] | CZE method[2] |
| 1 | 463 | 445 ± 28 |
| 2 | 177 | 185 ± 24 |
| 3 | 231 | 268 ± 29 |
| 4 | 404 | 424 ± 27 |
| 5 | 216 | 206 ± 23 |
| 6 | 498 | 428 ± 24 |
| 7 | 204 | 270 ± 27 |
| 8 | 386 | 376 ± 25 |

[1]The data came from Department of Nutritional Science, University of Connecticut.
[2]The data were the mean of 5 analysis ± standard deviation of the mean.

Linear regression (forced through the origin) of the correspondence between the two methods gave slope 0.981 with standard deviation 0,041 (i.e., not statistically different from 1) with correlation coefficient 0.925. The average coefficient of variation (standard deviation divided by mean) for CZE analysis was 1.5%. However, the CZE method is much faster and easier than the HPLC method.

EXAMPLE 2

HPCZE AND DRIED BLOOD SPOT SAMPLES

Serum and Blood Spot Sample Preparation:

All fasting blood samples were obtained from volunteers in Northeast Missouri State University and Kirksville College of Osteopathic Medical Center. After clotting at room temperature in the dark, sera were prepared by Centrifugation. The blood spots were prepared by spotting the vein blood or finger-prick blood on 903 special filter papers (Schleicher & Schuell, Keene, N.H., USA) immediately after the blood was drawn. The blood was allowed to dry and then analyzed for retinol levels.

Pretreatment of Blood Spot Sample:

The blood spot on the filter paper was cut off from the center with a ¼ inch diameter paper hole puncher, and was put into a 1.5 mL microcentrifuge tube and 300 µL ice-cold sample pretreatment buffer was added. Then the mixture was mixed on a Vortex mixer for 3–5 min *uncontinuously) until the blood spot was dissolved in the buffer completely. Then 100 µL of the blood spot solution was taken and filtered in the same way as that of serum sample. The filtrates were ready for HPCE analysis.

Pretreatment of Serum Samples:

To 10 µL serum, 290 µL ice-cold sample pretreatment buffer was added, and the mixture was mixed well on a Vortex mixer (Fisher, St. Louis, Mo, USA). The solution was allowed to stand on ice for 3–5 min, and 100 µL solution was taken out and put into a Microcon-30 filter unit (Amicon, Inc., Beverly, Mass., USA) (this filter unit allows molecular weight <30 KDa molecules to pass through), and filtrated by centrifugation. The filtrate was ready to be injected into HPCE column for analysis.

HPCZE Analysis:

Pretreated serum samples were injected electrokinetically at 10 kV for 10 s (approximately 8–10 nl was injected), and the separation was carried out at 20 kV for 5–6 minutes. The electrophoretic current was monitored with a multimeter throughout the separation to ensure the reproducibility. After each run, the capillary was washed with running buffer.

Conventional Extraction and HPLC Analysis of Retinol From Serum:

To 100 µL freshly thawed serum was added an equal volume of methanol containing an internal standard (retinyl acetate); each sample was extracted three times with an equal volume of hexane. Hexane from combined hexane extracts was evaporated under a gentle stream of Argon, and the residue was dissolved in 25 µL 2-propanol:dichloromethane (4:1 by volume; 20 µL was injected for HPLC analysis. Samples were analyzed by reversed-phase HPLC on a Resolve 5- µm $c_{18}$ column (Waters Associates, Milford, Mass.) using a mobile phase of methanol:water (95:5) at a flow-rate of 1.0 ml/min, with detection at 325 nm (25).

Quantification of Retinol in Dried Blood Spot:

There are two ways to quantify the retinol in the dried blood spot. In the first method, a calibration curve was set up with a series of standard blood spots whose serum Vitamin A concentration were known (analyzed by conventional HPLC method). Then the concentration of unknown blood spots can be found from the calibration curve. The second, one single blood spot, whose retinol concentration was quantified by HPLC, was used to make a calibration curve by diluting to different concentration of retinol after filtration. The Vitamin A concentration of unknown blood spots also can be found out from the calibration curve.

Figure 4:
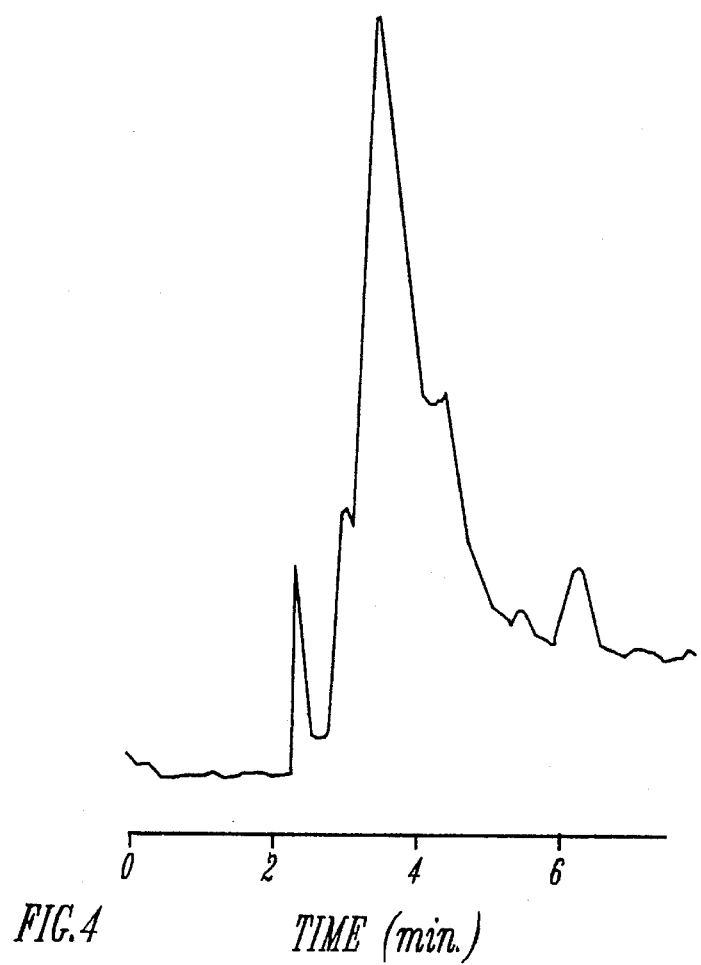

FIG. 4 shows the electrophoregram for direct injection of the dissolved blood spot sample without filtration under the current electrophoretic conditions. It is clear that it is impossible to determine retinol quantitatively. This is mainly caused by capillary wall adsorption of proteins and other molecules from the blood (the blood cells were broken during the dissolving process). Therefore, we adopted a membrane filter unit to get rid of most of the large size molecules from the blood sample. This step greatly reduced the wall adsorption problem and increased the reproducibility. The capillary was washed with running buffer between runs. The function of 6M urea is to totally dissociate plasma transthyretin (TTR) from retinol-RBP. This sample pretreatment step can also be applied to serum samples. The electrophoregram in FIG. 2 shows the separation of retinol-RBP in the pretreated serum sample. It can be seen that the matrix affects have been greatly decreased and the peak can be accurately integrated by integrator. We need to point out that the first peak in FIG. 5 was not coming from serum sample. We have done a blank control experiment, which allowed only pretreatment buffer to be filtrated with the filter unit by the same way with that of the blood sample, we still got that first peak, shown in FIG. 6. It was proven that the first fluorescence signal came from the filter unit.

Figure 7:
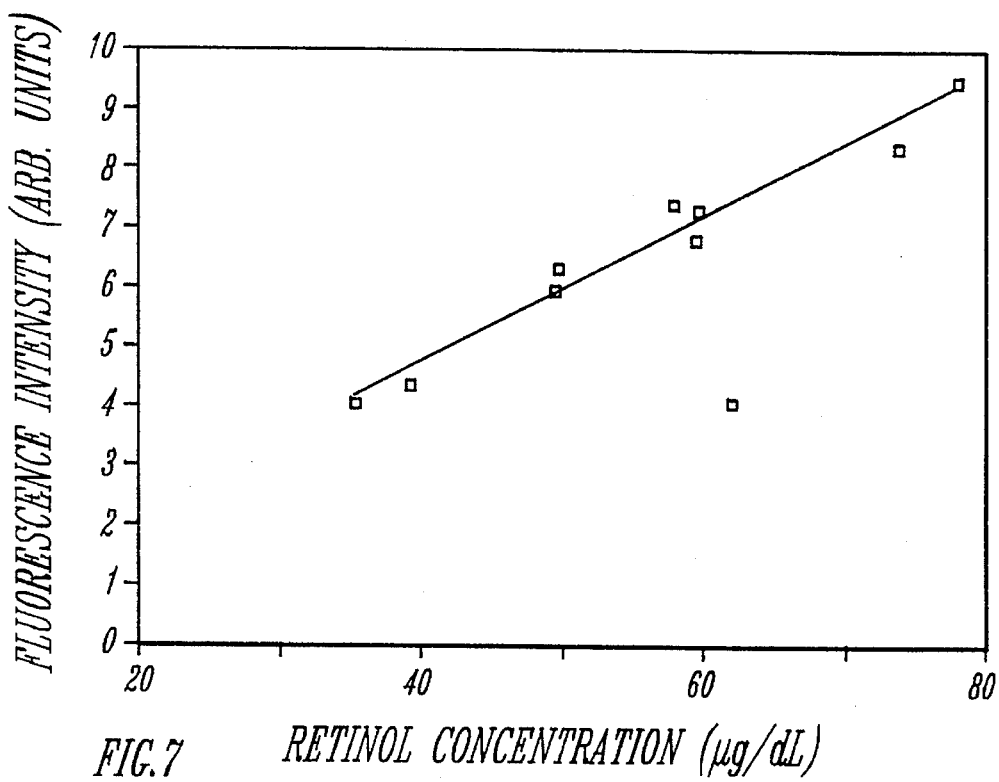
FIG. 7 shows the calibration curve for 10 serum samples (the concentrations retinol were determined by conventional HPLC).
Figure 8:
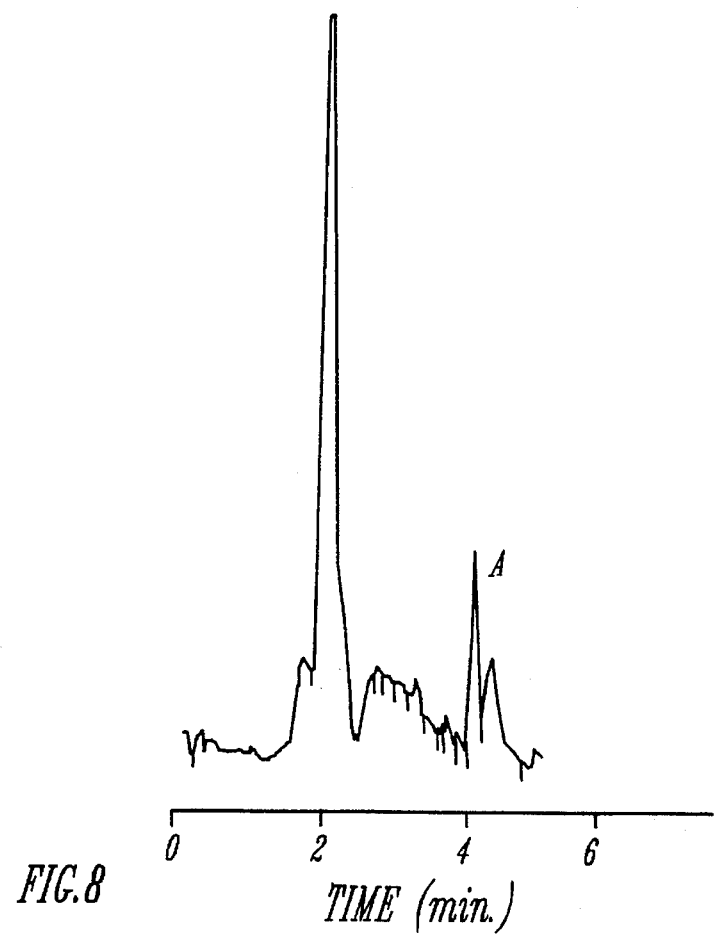
FIG. 8 shows the electrophoregram for the serum sample showing a lower result than that of HPLC. The electrophoretic conditions are the same as those of FIG. 4.

FIG. 7 shows the calibration curve from 10 serum samples. The concentration of retinol has been determined with HPLC. The calibration curve was made with the sera whose vitamin A concentrations are known. When these sera are injected into the HPCE column, the higher concentration of vitamin A will give a higher signal (i.e., will give a larger peak area), the lower concentration of vitamin A will give a smaller signal. Based on these peak areas according to different vitamin A concentration, a curve of responding signal (peak area) vs vitamin A concentration can be made. When an unknown serum sample is injected for analysis, a peak area of retinol-RBP for this serum sample can be obtained. From the calibration curve, we can find out the concentration of vitamin A corresponding to this peak area in this unknown serum sample. It can be seen that 9 samples show a linear response between fluorescence signal (peak area) and retinol concentration. However, one sample shows a much lower signal than other serum samples. The electrophoregram for this sample was also a little different from others (it was shown in FIG. 8), and a peak shows up right after the retinol-RBP peak. This could be due to human variability because some people may have different retinol metabolism and may have another retinol transport protein in serum.

Figure 9:
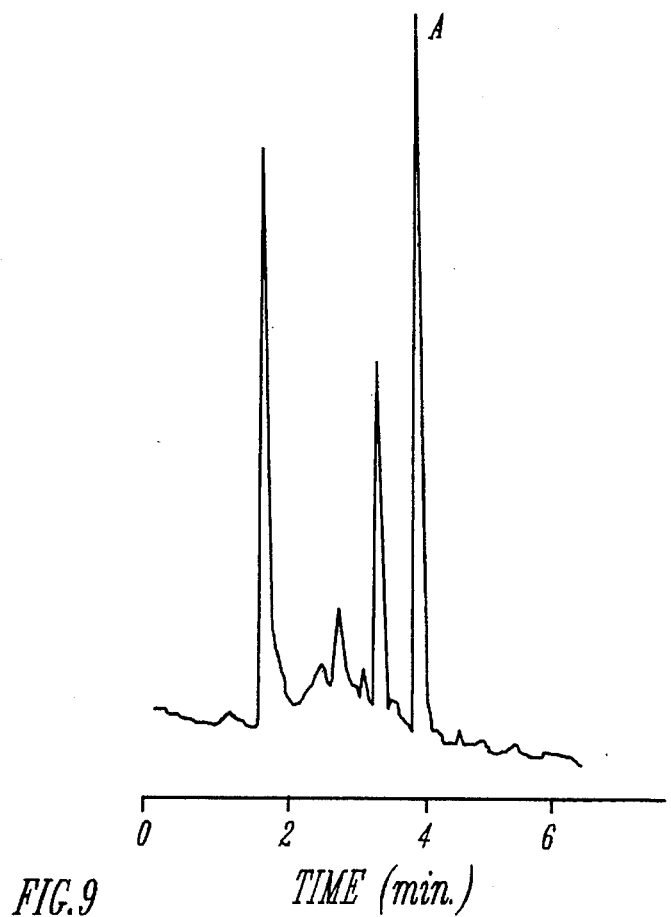
FIG. 9 shows electrophoregram of pretreated dried blood spot. The electrophoretic conditions are the same as those of FIG. 4.
Figure 10:
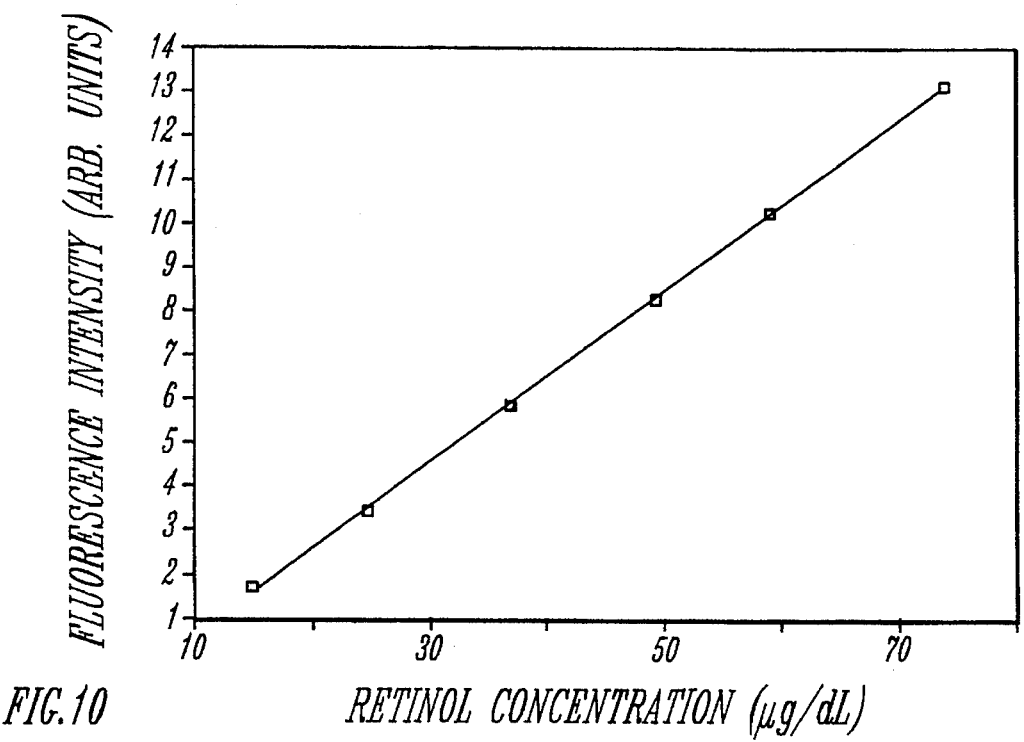
FIG. 10 shows the calibration curve for determining the retinol concentration in dried blood spot by using one blood spot with standard dilution. The electrophoretic conditions are the same as those of FIG. 4.

FIG. 9 shows the separation of retinol-RBP from dried blood spot. It can be seen that more peaks were observed from blood spot samples than the serum samples. This means that some molecules in the non-serum component of the blood spot may also fluoresce at the same wave length as that of retinol-RBP. In order to quantify the retinol in the dried blood spot, we used one blood spot, whose serum retinol concentration has been determined by using HPLC, to make a calibration curve by diluting to different concentration, the curve was shown in FIG. 10. The concentration of other blood spot samples can be found out from this calibration curve. Table II shows the retinol concentration of 10 blood spot samples found out from the calibration curve, and comparison to the value found out from HPLC.

TABLE II

Comparison of results between HPLC and HPCE for blood spot retinol analysis (Notes: the HPCE results were found from the HPCE calibration curve)

| Sample # | Retinol Concentration by HPLC | Retinol Concentration by HPCE |
|---|---|---|
| 1 | 73.8 | 73.7 |
| 2 | 35.2 | 39.0 |
| 3 | 39.2 | 39.8 |
| 4 | 49.4 | 55.1 |
| 5 | 62.0 | 33.8 |
| 6 | 78.0 | 79.3 |
| 7 | 49.6 | 53.0 |
| 8 | 59.4 | 58.8 |
| 9 | 59.6 | 65.0 |
| 10 | 57.8 | 60.7 |

It is clear that 9 blood spot samples match with the HPLC data well and one blood spot sample was off, this affect was also seen in the serum data. Since the 10 serum samples and 10 blood spot samples were coming from the same 10 people, we can see that the results from blood spots were very close to those of serum samples.

In order to quantitatively determine the retinol in dried blood spot, we have done a recovery study from 903 filter paper. A known volume of serum was spotted on the filter paper. After being dried, the whole spot was cut off and treated the same way as those of blood spot and analyzed by HPCE. Same volume of serum was taken and analyzed by HPCE without spotting on the filter paper. The recovery was calculated based on the peak area. The recoveries of seven serum samples are listed in Table III, with a range of 89% to 113%.

TABLE III

Recovery study of retinol in dried blood spot by high performance capillary electrophoresis

| blood spot sample | percent recovery |
|---|---|
| 1 | 113.5 |
| 2 | 107.6 |
| 3 | 98.6 |
| 4 | 90.1 |
| 5 | 99.6 |
| 6 | 96.8 |
| 7 | 89.0 |

From Table III we can see that for 7 samples studied, 6 of them have a percentage recovery over 96%. If an increase in the stirring time would help achieve even higher blood spot recovery in the pretreatment buffer.

From the above examples, it can be seen that the invention accomplishes at least all of its stated objectives.

What is claimed is:

1. A method for directly measuring the retinol concentration of a blood serum sample of 8–10 nl which comprises the steps of:

(a) collecting a sample of serum, said serum obtained from a blood sample;

(b) pretreating said serum sample to dissociate transthyretin from a TTR-retinol-RBP complex;

(c) separating said serum sample through a capillary by electrophoresis through a capillary said electrophoresis including a running buffer with a pH in the range of from about 7.5 to about 10.3;

(d) exciting said sample with an emission source at 325 nm (e) collecting and measuring the fluorescence given off by said separated sample (f) converting said fluorescence measurement to grams of retinol per liter.

2. The method of claim 1 where the analysis time is less than 6 minutes.

3. The method of claim 1 where the blood serum is human blood serum.

4. The method of claim 1 wherein said pretreatment includes treatment with a buffer comprising $Na_2HPO_4$ and urea.

5. The method of claim 1 wherein said running buffer comprises $Na_2HPO_4$ adjusted to a pH Of 7.8 with $H_3PO_4$.

6. The method of claim 1 wherein said emission source is a laser.

7. The method of claim 7 wherein said laser is composed of helium and cadmium.

8. The method of claim 1 wherein said fluorescence is collected and measured by means of a photodiode.

9. The method of claim 8 wherein said photodiode comprises silicon.

10. A method of evaluating serum retinol levels from a dried blood spot sample comprising:

dissolving said dried blood with a buffer to dissociate transthyretin from TTR-retinol-RBP complex;

separating serum from said dissolved blood;

separating said serum by electrophoresis through a capillary with a running buffer having a pH of between 7.5 and 10.3;

exciting said sample with a helium cadmium laser emission source at 325 nm;

collecting and measuring the fluorescence at a wavelength of 465 nm given of by said sample; and converting said fluorescence level to grams/liter.

11. The method of claim 10 wherein the sample amount is 8–10 nl.

12. The method of claim 10 where the analysis time is less than 6 minutes.

13. The method of claim 10 where the blood serum is human blood serum.

14. The buffer of claim 10 wherein said running buffer has a pH of 7.8.

15. The method of claim 10 where in said fluorescence is collected and measured by means of a photodiode.

16. The method of claim 15 wherein said photodiode comprises silicon.

* * * * *